US 6,659,103 B2

(12) United States Patent
Tiemens

(10) Patent No.: US 6,659,103 B2
(45) Date of Patent: Dec. 9, 2003

(54) EARPLUG WITH STIFFENER

(75) Inventor: Jim Tiemens, Laguna Nigel, CA (US)

(73) Assignee: Bacou-Dalloz USA Safety, Inc., San Diego, CA (US)

(*) Notice: Subject to any disclaimer, the term of this patent is extended or adjusted under 35 U.S.C. 154(b) by 0 days.

(21) Appl. No.: 10/212,284

(22) Filed: Aug. 1, 2002

(65) Prior Publication Data
US 2003/0029459 A1 Feb. 13, 2003

Related U.S. Application Data
(60) Provisional application No. 60/311,610, filed on Aug. 10, 2001.

(51) Int. Cl.[7] ................................. A61F 11/00
(52) U.S. Cl. ....................... 128/864; 181/135
(58) Field of Search ................ 128/864–868; 181/130, 135

(56) References Cited

U.S. PATENT DOCUMENTS

| | | | |
|---|---|---|---|
| 2,538,339 A | * | 1/1951 | Thomas ........................ 128/151 |
| D253,723 S | | 12/1979 | Leight |
| 4,434,794 A | | 3/1984 | Leight |
| 5,188,123 A | | 2/1993 | Gardner, Jr. |
| 5,249,309 A | | 10/1993 | Berg et al. |
| 5,573,015 A | | 11/1996 | Williams |
| 5,799,658 A | | 9/1998 | Falco |
| 5,811,742 A | | 9/1998 | Leight |
| 6,006,857 A | | 12/1999 | Leight et al. |
| 6,264,870 B1 | * | 7/2001 | Hakansson ................... 264/255 |

* cited by examiner

Primary Examiner—Michael A. Brown
(74) Attorney, Agent, or Firm—Leon D. Rosen

(57) ABSTRACT

An earplug includes a body of soft elastomeric material such as a soft resilient foam for insertion in the ear canal, and a stiffener of more rigid material than the body. The stiffener is in the form of a tube rather than a solid rod, so while the stiffener is resistant to column-like collapse, it is easily radially compressed to facilitate compression of the body as it enters the ear canal. The stiffener tube can be filled with soft resilient foam material, to block the passage of sound through the tube. The tubular stiffener can have a slot extending parallel to the length of the stiffener, to allow soft foam material to flow into the tube to fill it, as the foam material that surrounds the tube is molded. Such molding can be accomplished by extruding foam material while the tubular stiffener passes with the extruded foam through the extrusion head.

13 Claims, 2 Drawing Sheets

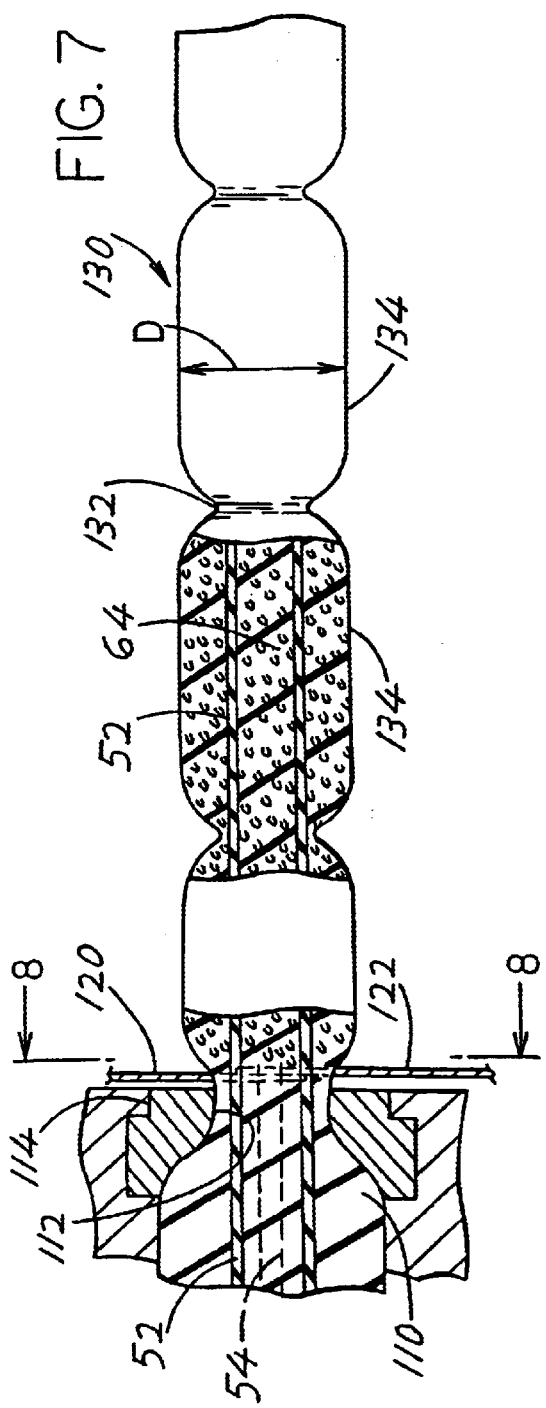

EARPLUG WITH STIFFENER

CROSS-REFERENCE TO RELATED APPLICATION

Applicant claims priority from U.S. Provisional Patent Application 60/311,610 filed Aug. 10, 2001.

BACKGROUND OF THE INVENTION

One common type of earplug includes a cylinder punched out of a plate of elastomeric polymer foam material, or a bullet-shaped member molded of such polymer foam material. It is difficult to insert the front portion of an ordinary foam earplug into the ear canal, because the rear end of such earplug collapses as it is pushed forward in an attempt to insert the front portion into the ear canal. As a result, such earplugs of foam are commonly formed of slow recovery material which can be rolled between the fingers to a small diameter and inserted into the ear canal and held therein while the front end of the earplug expands during a period of perhaps 30 seconds. If a worker's hands are dirty, then the rolled earplug will pick up dirt, which is a disadvantage of such earplugs.

Another type of earplug, such as shown in U.S. Pat. Nos. 4,434, 792 and 5,573,015, includes a body of resilient foam or very soft solid rubber molded with an axial passage, and a stiffening rod of more rigid material lying in the passage. The stiffening rod resists column-like collapse, and pushes the front end of the body into the ear canal. The stiffening rod has a disadvantage in that it makes the front end of the body stiffer against radial compression so greater force is required to insert the body front end into the ear canal and the earplug is not as comfortable. An earplug that could be constructed at low cost, which could be installed in the ear canal without requiring rolling between the fingers, and which had a front body portion that was easily radially compressed for easy of installation and comfort, would be of value.

Many earplugs are constructed in pairs that are connected by a cord. Such cords are commonly attached to an earplug by forcing an end of a cord into the earplug, with adhesive on the cord end bonded to the earplug. If the earplug is of soft foam, such insertion may be difficult. In practice, the cord is often inserted off center from the earplug axis and sometimes comes out when pulled to take out the earplug. It would be desirable if an earplug were constructed that facilitated reliable and accurately on-axis installation of a cord end in the earplug.

SUMMARY OF THE INVENTION

In accordance with one embodiment of the present invention, an earplug is provided with a body front portion that can be inserted into the ear canal to seal thereagainst, and a stiffener that preferably lies within the body front portion to stiffen the earplug against column-like collapse, wherein the stiffener is easily radially compressed. The stiffener is in the form of a tube, which provides high resistance to column-type collapse, but which can be easily radially compressed. The body of soft elastomeric material is molded and the tubular stiffener may be molded integrally with the body. In most cases, the body is formed of a soft foam material and the inside of the tubular stiffener is filled with soft foam material. Simultaneous molding of the body and material within the tubular stiffener, is facilitated by forming the stiffener with a slot extending parallel to its length, so material can pass from around the tubular stiffener and through the slot to fill the inside of the tubular stiffener with the same foam material that forms the body of the earplug.

Earplugs of the above type can be molded by extrusion of foamable material through a die head. The tubular stiffener can be passed through the middle of the die head opening, to result in an elongated extrusion comprising a tubular stiffener surrounded by soft foam material that is bonded around the outside of the stiffener. The elongated extrusion can be partially separated into individual earplugs by compressing and cutting the foamable material of the body prior to complete foaming and setting, resulting in a chain of connected earplugs. The chain can be stored and later cut into individual earplugs as needed, or the chain can be immediately cut into individual earplugs such as at the time when the foam material is compressed to separate foam material of sequential earplugs.

The tubular stiffener lying within soft elastomeric material, facilitates the production of specialized earplug pairs that are connected together by a cord. Such cord can be inserted into the tubular stiffener of each earplug of the pair and fixed in place as by adhesive. The fact that the stiffener provides a passage accurately centered on the axis of the earplug, results in the cord ends being more easily and reliably inserted into the earplug and lying more accurately on the axis of the earplug.

The novel features of the invention are set forth with particularity in the appended claims. The invention will be best understood from the following description when read in conjunction with the accompanying drawings.

BRIEF DESCRIPTION OF THE DRAWINGS

FIG. 7 is partially sectional side view showing a chain of earplugs and showing a method by which the chain of earplugs is manufactured.

FIG. 8 is a view of the pincher taken on line 8—8 of FIG. 7.

FIG. 9 is a partially sectional side view of an earplug of the chain of FIG. 7, which has been separated from other earplugs.

DESCRIPTION OF THE PREFERRED EMBODIMENTS

Figure 1:
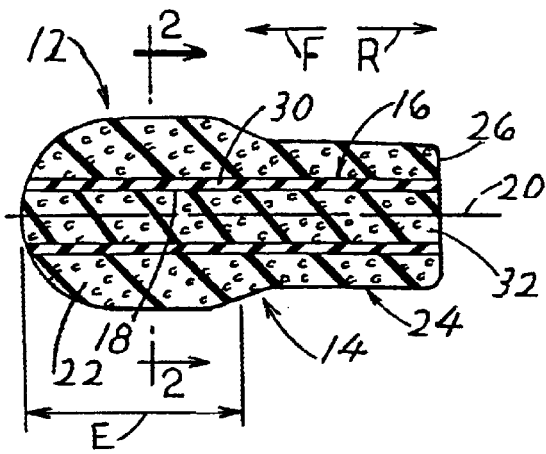
FIG. 1 is a sectional side view of an earplug constructed in accordance with one embodiment of the present invention.
Figure 2:
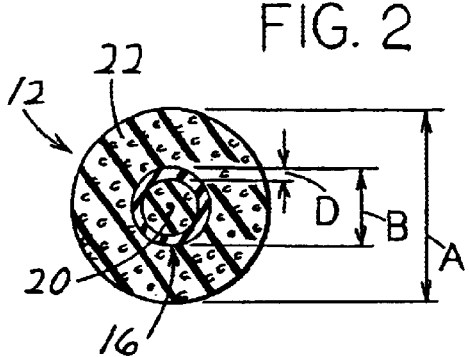
FIG. 2 is a sectional view taken on line 2—2 of FIG. 1.
Figure 3:
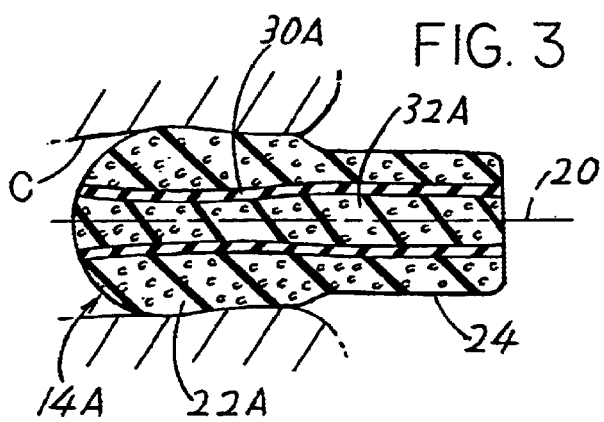
FIG. 3 is a view of the earplug of FIG. 1, shown inserted into an ear canal and with the front portion of the earplug radially compressed.

FIGS. 1–3 illustrate an earplug 12 that includes a body 14 of soft elastomeric material in the form of resilient foam, and a stiffener 16 that extends along the axis 20 of the body and that lies within a body passage 18 extending along the axis of the body. The body has front and rear sections, or portions 22, 24. The front portion 22 is designed to be inserted forwardly F into a person's ear canal, and to be radially (with respect to axis 20) compressed by the walls of the ear canal, so the body front portion forms a sound-tight seal against the walls of the ear canal to protect the wearer from loud sounds. The rear portion 24 is grasped between a person's fingers to push the front portion forwardly F into the ear canal and to pull the ear plug rearwardly R out of the ear canal.

The body 14 is formed of a soft foam material such as a low density (e.g. 2 grams/cm$^3$) of TPR (thermoplastic rubber). This allows the body front portion to be radially compressed as it is pushed into the ear canal. However, the high resilience of the material which allows it to be easily radially compressed when merely pushed into the ear canal, results in the rear portion 24 of the body having little resistance to column-like collapse when pushed. The stiffener 16 has at least a radially outer portion formed of material having a much greater stiffness than the resilient foam material of the body 14. The greater stiffness of the stiffener 16 allows a person to press forwardly against the rear end 26 of the earplug or push forwardly while grasping the rear portion 24, with the stiffener 16 resisting column-like collapse. The stiffener extends at least partially in the front portion, and preferably along at least half the length E of the body front portion 22, and is preferably bonded to the body so forward movement of the stiffener results in it dragging the body front portion 22 into the ear canal.

The stiffener 16 includes a tube 30 of material more rigid than the soft foam of the body 14. However, the tube 30 is formed of flexible material that can be easily radially (perpendicular to axis 20) compressed. A string-like part 32 lies within the tube 30 and blocks the passage of sound through the inside of the tube 30.

It is known to form an earplug with a resilient foam body and with a solid rubber or silicone core in the shape of a rod extending along the axis of the resilient body. An important advantage of applicant's tubular stiffener is that the stiffener is resiliently compressible in a radial direction, perpendicular to the axis 20. FIG. 3 shows the earplug after the front portion 22A of the earplug 14A, has been inserted into an ear canal C. Such insertion results in radial compression of the body front portion, which results in sealing of the body front portion against the walls of the ear canal to prevent the passage of sound between them and into the ear canal. Such compression of the body front portion at 22A, also results in compression of the stiffener tube to the configuration 30A. The soft foam string-like part 32A is also radially compressed.

Thus, the presence of a tubular stiffener instead of a solid rod stiffener, has an important advantage in that the tubular stiffener is resiliently compressible. The tubular stiffener is not quite as rigid against column-like collapse as a solid rod of the same material and same outside diameter. However, a solid rod resists column-like collapse (in which the rod bends when axial compression forces are applied between its ends) primarily as a result of material near the periphery of the rod, and the tubular stiffener is almost as stiff against column-like collapse as a solid rod of the same material and outside diameter. To increase rigidity against column-like collapse, applicant makes the tube 30 of slightly greater diameter. It is also possible to use slightly stiffer material to achieve the same resistance to column collapse with the same tube outside diameter.

An elastomeric material may be defined as one having a Youngs modules of elasticity of no more than 50,000 psi. The body 14 is formed of a resilient foam while the tubular stiffener 30 is preferably formed of an elastomeric material of at least twice the stiffness. It is possible to form the tubular stiffener 30 of a material that is not elastomeric but readily bends, although applicant prefers to use an elastomeric material. In an earplug of the construction illustrated in FIGS. 1–3, the body preferably has a durometer of 1 to 10, shore A. The tube 16 is of solid elastomeric material, such as a soft rubber, which has a durometer of at least 30 shore A. The durometer stiffness of the tube material is preferably at least twice that of the body. The outside and inside surfaces of the tube are bonded respectively to the body 14 and to the center part 30, usually as a result of the foam material foaming and setting while in contact with the tube. An examination of the finished earplug which is cut, shows this.

In the earplug shown in FIG. 2, the front portion 22 has an outside diameter A of between about 9 mm and 13 mm, so it is radially compressed when inserted into the ear canals of most people. The tube 16 has an outside diameter B that is preferably between 2 mm and 7 mm. A large diameter tube is desirable to resist column collapse using tube walls of small thickness D for high resilience to radial compression but decreases radial resilience of the earplug. At least about 1 mm of the soft foam material should lie around the tube so such material can be compressed to seal against the walls of the ear canal. The inside diameter of the tube is preferably chosen so the wall thickness D of the tube is no more than about half the radius B/2 of the tube to provide high resilience in radial compression.

Figure 4:
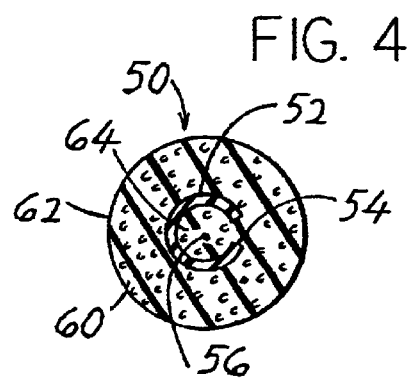
FIG. 4 is a sectional view similar to FIG. 2, but of an earplug of another embodiment of the invention, which facilitates its manufacturer.

The earplug of FIGS. 1–3 can be formed in several different ways. A basic approach is to first form the stiffener tube 30 and place it in a mold, with foamable liquid also placed in the mold around the tube and in the tube. FIG. 4 shows an earplug 50 similar to that of FIGS. 1–3, but with a stiffener tube 52 that has a gap 54 extending parallel to the axis 56 of the tube along the entire length of the tube. The purpose of the gap 54 is to allow material 60 in the body 62 that surrounds the tube, to flow into the inside of the tube and form the string-like part 64 that lies within the tube. The body 62 and string part 64 are connected by a portion of the material lying in the gap 54. The presence of the gap facilitates molding of the earplug, because it eliminates the need to pour or otherwise separately add soft compressible material to the inside of the tube 52.

Applicant prefers that the gap 54 extend by no more than 90° and preferably by no more than 60° to avoid a side that collapses much more readily than the rest. The gap generally must be at least 10° to allow material to flow into the inside of the tube and equalize the pressure of the foaming material.

Figure 5:
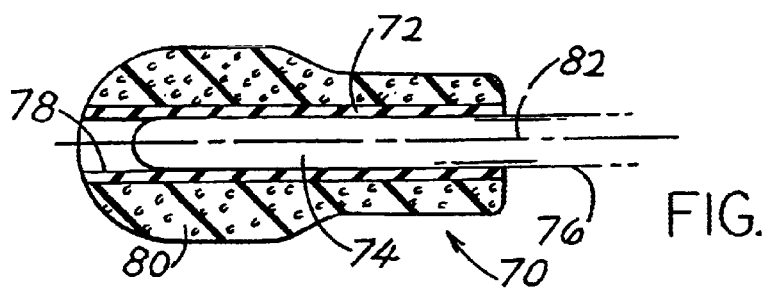
FIG. 5 is a sectional side view of an earplug of another embodiment of the invention, wherein an end of a cord is anchored in the earplug

FIG. 5 illustrates an earplug 70 similar to that of FIG. 1, but wherein the tube 72 is not filled with resilient foam material or the like. Instead, the tube 72 (preferably without a gap) is left hollow until one end 74 of a cord 76 is inserted into the tube. The inside of the tube and/or the outside of the cord end 74 can be coated with an adhesive which sets and bonds after the cord is inserted. The cord end 74 blocks the passage of sound. An end of the cord 76 opposite the end 74 is similarly installed in a tube of another similar earplug, to provide a corded pair of earplugs. The presence of a tube whose passage 78 is centered on the axis 82 of the earplug body 80, results in a cord being installed at the center of the earplug. This enhances the appearance and facilitates deep installation of the cord end.

Figure 6:
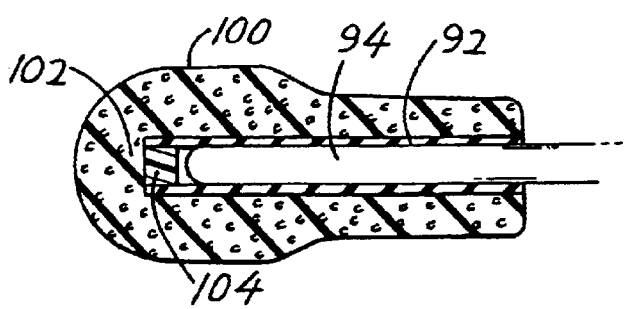
FIG. 6 is a sectional view similar to FIG. 5, of another embodiment of the invention wherein the end of a cord is anchored in the earplug.

FIG. 6 shows an earplug 90 similar to that of FIG. 5, except that the tube 92 projects only part of the way through the earplug body 100 and is sealed by a plug 104, with material at 102 being left forward of the tube to block sound. A cord end 94 lies in the tube.

FIG. 7 shows earplugs of the general type illustrated in FIG. 4, being manufactured by extrusion. A preformed continuous tube 52 with a gap 54 in it is passed through a mass 110 of foamable material which is still in a liquid state, to flow through an opening 112 in an extrusion head 114 along with the foamable material. As the foamable material flows out around the stiffener tube 52, the foamable material rapidly generates gas bubbles and expands in diameter to the final diameter D as it foams. It is possible to leave a continuous extrusion with a stiffener tube therein and cut it into individual earplugs each about once inch long. Applicant rounds the ends of the earplugs to form a chain 130 of individual earplugs 134 connected together largely by the tube 52 and the string-like part 64 within the stiffener tube. Applicant accomplishes this by a pair of pinching dies 120, 122 which rapidly pinch the extrusion close to where it emerges from the extrusion opening 112. The pinched locations on the extrusion form rounded ends (for the earplug following the pinch off and the earplug preceding the pinch off). In between earplugs, at 132, the thickness of the body around the tube is less than half the thickness at the middle of each earplug. The chain of earplug can be stored, and individual earplugs removed from the chain by cutting them at the intersection 132 of two earplugs that are connected in series. FIG. 9 illustrates one of such earplugs 134A.

Thus, the invention provides an earplug with an improved stiffener in the form of a tube that extends along the axis of the earplug and that resists column-like collapse when the rear end of the earplug is pushed forward to insert the front portion into the ear canal. The stiffener tube has a considerable diameter but thin walls, so the tube resists column-like collapse but does not greatly resist radially compression. As a result, the front portion of the earplug body that enters the ear canal and that must be compressed by the ear canal, is more easily compressed. The stiffener tube can be formed with a gap, especially an axially-extending gap, to facilitate forming the earplug by flowing a foamable material around the tube and allowing the foamable material to flow through the gap into the inside of the tube to fill it. The earplug with tube is also useful in the installation of the end of a cord in those devices that include a pair of earplugs connected by a cord. Multiple earplugs can be formed by extrusion, and locations along the extrusion can be pinched to form a string of earplugs with rounded ends that are connected by the tube.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Earplug apparatus for lying in a human ear canal, comprising:
   a tube of a first material that is flexible, said tube having an axis and front and rear tube portions spaced along said axis;
   a quantity of second material that is an elastomeric foam material and which forms a body that surrounds at least said front portion of said tube;
   a quantity of third material that is an elastomeric foam material and which fills at least said front portion of said tube;
   said first material having at least twice the stiffness of said second and third materials, said second material being molded around said tube, and said third material being molded in said tube.

2. The apparatus described in claim 1 wherein:
   said tube has an axially extending gap, and said second and third materials are the same and are joined through said gap.

3. The earplug apparatus described in claim 1 wherein:
   said quantity of second material forms a plurality of body sections that includes said body and that lie in series and that have adjacent ends that are primarily separated from one another, said tube extends continuously through a plurality of said body sections to hold them connected in series.

4. A method for forming an earplug that has an axis and that can be easily inserted into the ear canal and radially compressed during such insertion, to block noise, comprising:
   molding a second elastomeric material around a tube of a first elastomeric material, wherein said first material has a greater rigidity than said second material;
   molding a third elastomeric material in the inside of said tube, wherein said first material has a greater rigidity than said third material.

5. The method described in claim 4 wherein:
   said second and third materials are each foam, while said first material is a solid elastomeric material that is substantially devoid of gas bubbles.

6. The method described in claim 4 wherein:
   said tube has an axis and has an axially-extending gap, said second and third elastomeric material are the same, and said steps of molding second and third elastomeric materials includes molding said second elastomeric materials around said tube and allowing some of said second elastomeric material to pass into said tube through said gap.

7. Earplug apparatus for lying in a human ear canal, comprising:
   a body of elastomeric first material with a front portion to be compressed in diameter as it is pushed into the ear canal to block sound, and a rear end, said body having an axis;
   a stiffener of material more rigid than said first material and of smaller outside diameter than said front portion, said stiffener lying in said body and extending along said axis to stiffen said earplug against column type collapse when said earplug is pushed into the ear canal;
   said stiffener being in the form of a tube filled with elastomeric material that is more resilient than material of said tube.

8. The apparatus described in claim 7 wherein:
   said elastomeric material in said tube is said first material, and said tube has an axially-extending slot to allow the flowthrough of said material into said tube during manufacture.

9. The apparatus described in claim 7 wherein:
   said elastomeric material which fills said tube is molded in said tube at the same time as said body is molded.

10. Earplug apparatus for lying in a human ear, comprising:
    a plurality of identical earplugs that lie in series with one another
    each of said earplugs comprises a body of elastomeric first material with a front portion to be compressed in diameter as it is pushed into the ear canal to block sound, and a rear end, said body having an axis and a stiffener of material more rigid than said first material and of smaller outside diameter than said front portion, said stiffener being in the form of a tube and lying in said body and extending along said axis to stiffen said earplug against column type collapse when said earplug is pushed into the ear canal;

said tube stiffener extending continuously in series between said earplugs but with the bodies of adjacent earplugs being substantially separated from one another.

11. Earplug apparatus for lying in a human ear canal comprising:
  a body of elastomeric first material with a largely cylindrical front portion to be compressed in diameter as it is pushed into the ear canal to block sound, and a rear end, said body having an axis;
  a stiffener of material more rigid than said first material and of smaller outside diameter than said front portion, said stiffener being in the form of a tube and lying in said body and extending along said axis to stiffen said earplug against column type collapse when said earplug is pushed into the ear canal;
  said front portion outside diameter is at least 9.4 mm and said tube has a constant outside diameter of between 2 mm and 7 mm.

12. Earplug apparatus for lying in a human ear canal, comprising:
  a body of elastomeric resilient foam first material that has multiple gas bubbles, said body having a front portion to be compressed in diameter as it is pushed into the ear canal to block sound, and a rear end, said body having an axis;
  a stiffener of material more rigid than said first material and of smaller outside diameter than said front portion, said stiffener lying in said body and extending along said axis to stiffen said earplug against column type collapse when said earplug is pushed into the ear canal;
  said stiffener being in the form of a tube of a second elastomeric material that is substantially devoid of gas bubbles and which has more than twice the stiffness of said first material.

13. Earplug apparatus for lying in a human ear canal, comprising:
  a body of elastomeric first material with a front portion to be compressed in diameter as it is pushed into the ear canal to block sound, and a rear end, said body having an axis;
  a stiffener of material more rigid than said first material and of smaller outside diameter than said front portion, said stiffener being in the form of a tube and lying in said body and extending along said axis to stiffen said earplug against column type collapse when said earplug is pushed into the ear canal;
  a cord having opposite ends;
  one of said cords ends lies in said tube and is fixed in place therein.

* * * * *